United States Patent [19]

Minato et al.

[11] 4,116,774

[45] Sep. 26, 1978

[54] METHOD FOR THE DETERMINATION OF ENZYME ACTIVITIES

[75] Inventors: Sadamasa Minato; Atsushi Hattori; Yoshihiko Baba; Yuichiro Yabe; Seigo Ueda, all of Hiromachi, Japan

[73] Assignee: Sankyo Company Limited, Tokyo, Japan

[21] Appl. No.: 798,938

[22] Filed: May 20, 1977

[30] Foreign Application Priority Data

Jun. 1, 1976 [JP] Japan .................................. 51-63786

[51] Int. Cl.$^2$ ...................... G01N 33/00; G01N 31/14
[52] U.S. Cl. .................................. 195/99; 195/103.5 R
[58] Field of Search ........................... 195/99, 103.5 R

[56] References Cited

U.S. PATENT DOCUMENTS 3,769,173  10/1973  Carroll ........................... 195/103.5 R
3,892,631  7/1975  Carroll ........................... 195/103.5 R

OTHER PUBLICATIONS

Goldbarg et al., Arch. Biochem. & Biophysics 91, (1960) pp. 61–70.

Primary Examiner—Raymond N. Jones
Assistant Examiner—C. A. Fan
Attorney, Agent, or Firm—Toren, McGeady and Stanger

[57] ABSTRACT

Improvement in determination of an enzyme activity in a substance having an enzymatic activity which comprises employing an aromatic primary amine derivative as a substrate and an iron complex treated with a peroxide as a color reagent.

6 Claims, No Drawings

METHOD FOR THE DETERMINATION OF ENZYME ACTIVITIES

BRIEF SUMMARY OF THE INVENTION

This invention relates to a new and improved method for the determination of an enzyme activity in a substance having an enzymatic activity and, more particularly, to a new method for the determination of an enzyme activity which comprises employing a derivative of an aromatic primary amine as a substrate for determining an enzyme activity and a novel stable iron complex reagent to make a color development.

DETAILED DESCRIPTION

Such substances having an enzymatic activity as serum, saliva, cerebrospinal fluid, urine, gastric juice and the like among body fluids have been applied as various diagnostic samples. Taking the case of serum for illustration, it is known that an activity of such enzyme as peptidase, transpeptidase etc. found in serum be remarkably variable depending upon physiological and diseased conditions of a living body. For instance, γ-glutamyltranspeptidase (hereinafter referred to as γ-GTPase) and leucineaminopeptidase (hereinafter referred to as LAPase) have been widely employed for diagnosis of hepatic diseases, while cysteineaminopeptidase (hereinafter referred to as CAPase) has been used for diagnosis of placental function upon pregnancy and they have provided important diagnosis methods. It is usually admitted that a colorimetric determination of a component in a living body be practicable without any influence caused by pigments in a living body if the wave length to be applied for determination is not less than 600 nm. For determination of an enzymatic activity of peptidase, transpeptidase and the like, there have generally been proposed a method wherein a derivative of p-nitroaniline is employed as a substrate and yellow-colored p-nitroaniline liberated from enzymatic reaction is colorimetrically determined and another method wherein β-naphthylamine liberated from enzymatic reaction is made yellow to red-colored with a diazo reaction for determination. However, yellow pigments may be included in serum or serum is colored red when partly hemolyzed and hence the measured value may be influenced upon serum component when measured by any publicly known methods. It is, therefore, a great need to develop a method in which a colorimetric determination is practicable within a long wavelength region of not less than 600 nm.

As a result of our earnest studies in order to diminish these defects, it has been found that an enzyme activity in serum can be determined without any influence caused by other components in serum by using a derivative of an aromatic amine as a substrate and making the aromatic amine, which is liberated from an enzymatic reaction, blue — or bluish green — colored with an iron complex. It is to be noted that the present method is applicable to determination of an enzyme activity not only in serum but also in other substances having any enzymatic activity.

It is reported in Mikrochimica Acta, 2, page 3 (1937) that an aromatic amine, particularly a primary amine is blue — or green — colored with a reagent derived from a pentacyanoammineferroate by treatment with bromine water. However, this reagent is not employable as a reagent for quantification and so unstable as to produce precipitates during storage and it has been unable to be employed as a practical diagnosis reagent. As a result of our further extensive studies to diminish these defects, it has been discovered that a stable color reagent for an aromatic amine with a quantitative coloring ability can be prepared by treating a pentacyanoammineferroate with a peroxide.

As the pentacyanoammineferroate which may be employed in this invention, there may be mentioned sodium or potassium pentacyanoammineferroate. Also, as the peroxide which may be employed in this invention for the peroxide treatment, there may be suitably mentioned sodium periodate, potassium periodate, potassium permanganate, hydrogen peroxide and the like, with hydrogen peroxide being most preferable.

The aromatic primary amine derivatives which may be employed as a substrate in the present invention are contemplated to include, for example, the following derivatives.

| No. | Chemical Name | Structure |
|---|---|---|
| 1 | L-glutamic acid γ-p-dimethylaminoanilide | 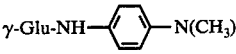 |
| 2 | L-glutamic acid γ-p-diethylaminoanilide | 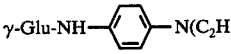 |
| 3 | L-glutamic acid γ-p-methoxyanilide | 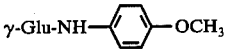 |
| 4 | L-glutamic acid γ-p-hydroxyanilide | 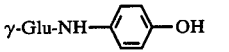 |
| 5 | S-benzyl-L-cysteine p-dimethylaminoanilide | 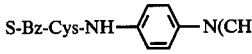 |
| 6 | S-benzyl-L-cysteine p-hydroxyanilide | 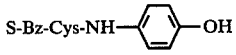 |
| 7 | S-benzyl-L-cysteine p-methoxyanilide | 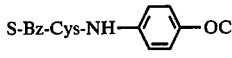 |
| 8 | L-leucine p-dimethylaminoanilide | 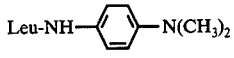 |
| 9 | L-leucine p-hydroxyanilide | 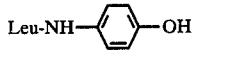 |
| 10 | L-leucine p-methoxyanilide | 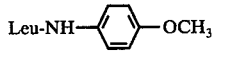 |
| 11 | N-benzyl-L-tyrosine p-dimethylaminoanilide | 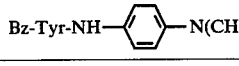 |

The amine derivatives having the above Nos. 1, 2, 3 and 4 are all new substances and can be prepared according to the teaching in our Japanese Patent Application No. 63783/1976 (filed on June 1, 1976) and those having the above Nos. 5, 6, 7, 8, 9 and 10 are also new substances and can be prepared according to the teaching in our Japanese Patent Application No. 63784/1976 (filed on June 1, 1976). The amine derivative of the above No. 11 is a new substance and can be prepared according to the teaching in our Japanese Patent Application No. 63785/1976 (filed on June 1, 1976).

As a practically suitable embodiment, a far more stable iron complex reagent can be prepared by blending the iron complex with an alkali metal hydrogencarbonate, e.g., sodium hydrogencarbonate, lithium hydrogencarbonate, potassium hydrogencarbonate and a low molecular dextran. The iron complex of such a reagent blend becomes very stable when freeze-dried and it is, accordingly, preferable to make up the blend in the form of a freeze-dried preparation when formulated as a reagent for color reaction.

Also, in cases where the present color reaction is to be applied for determination of an enzyme activity in serum, a color developement in such a publicly known alkaline solution as shown in the above-named literature may be significantly influenced with a contaminating serum and then it becomes difficult to find out a linear relationship beweem an amount of the amine to be determined and the measured absorbance, which results in very disadvantageous defects in determination of an enzyme activity. It is desirable for covering this defect to employ a weakly acidic buffer upon color development. The pH of a buffer to be employed is 3.0–7.0, with the most preferable pH being 4.0–5.5. Also, in regard to the kind of a buffer, one may employ all weakly acidic buffers usually employed, but a buffer comprising lactic acid, citric acid, oxalic acid, etc. is most preferable. A concentration of the buffer is 0.01–1 mole and 0.05–0.4 mole is most preferable.

In determination of an enzyme activity according to the present method, the aromatic amine derivatives are selected and employed as a substrate for individual enzymes to which said selected amine derivatives are specifically adaptable. For instance, a γ-L-glutamyl derivative is employed for determination of γ·GTPase, an S-benzyl-L-cysteinyl derivative for determination of CAPase and an L-leucyl derivative for determination of LAPase, respectively. After an enzymatic reaction is effected between individual substrate and serum for 30 minutes, the aromatic amine thus liberated is measured by color development with the said reagent. As the aromatic amines liberated from these reactions, there may be mentioned the following.

sodium pentacyanoammineferroate are summarized in Table 1.

Table 1.

| Coloration of various aromatic amines | | |
|---|---|---|
| Amine | λ max (nm) | OD 660* |
| p-anisidine | 695 | 0.51 |
| p-aminodiphenylamine | 655 | 0.62 |
| Valiamine Blue B Salt | 655 | 0.38 |
| 8-aminoquinoline | 660 | 0.18 |
| N,N-dimethyl-p-phenylenediamine | 700 | 0.58 |
| N,N-diethyl-p-phenylenediamine | 700 | 0.58 |
| p-aminophenol | 700 | 0.52 |

*Absorbance when 0.2 mM amine soln. colored

It is, accordingly, noted that an enzyme activity can be determined in a long wavelength region without any interference from other substances by the use of the present method.

As one embodiment according to the present invention, practical coloration procedures may be conducted as shown below: Namely, 1 volume of a color reagent containing the said iron complex is dissolved in 50 volume of a 0.2 mole buffer (pH 4.5) containing 1.0% of sodium chloride or potassium chloride to form a reaction stopping and coloring solution and five times volume thereof is added to an enzyme reaction solution. The mixture is left at room temperature for 20 minutes and colorimetrically determined. In cases where an enzyme activity in serum is to be determined, a sample as a blank for a reagent is measured which is treated and color-developed in the same manner by using water instead of the serum and then an acitivity can be represented with a difference in absorbance (Δ OD) between the measured value when serum is employed and the p-Anisidine

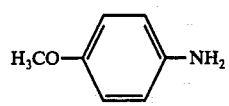

p-Aminodiphenylamine

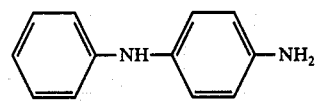

Valiamine Blue B Salt

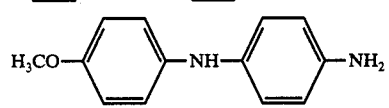

8-Aminoquinoline

N,N-Dimethyl-p-phenylenediamine

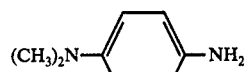

N,N-Diethyl-p-phenylenediamine

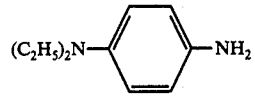

p-Aminophenol

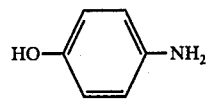

Wavelength and absorbance measured on the above-listed aromatic amines colored with a peroxide-treated measured value on the above sample. The coloring solution is colored blue to bluish green, which is determined in a long wavelength region of not less than 600 nm. Any influence upon pigments in serum is, therefore, not observed at all, neither is detected coloration of serum itself. Thus, even in cases where multiple serum samples are to be determined, only a reagent blank using water is satisfactory for a control test. Several examples of the results of the enzyme activities measured as set forth above are summarized in Table 2.

Table 2.

| Enzyme activities using various aromatic amine derivatives as substrate (37° C) | | | |
|---|---|---|---|
| Enzyme | Substrate | Km | V max |
| *1 | γ-Glu-NH—⟨C₆H₄⟩—N(CH₃)₂ | 0.55 mM | 1.00** |
| | γ-Glu-NH—⟨C₆H₄⟩—N(C₂H₅)₂ | 0.83 | 0.70 |
| γ-GTPase | γ-Glu-NH—⟨C₆H₄⟩—OH | 0.75 | 0.39 |
| | γ-Glu-NH—⟨C₆H₄⟩—OCH₃ | 0.75 | 0.37 |
| *2 | S-Bz-Cys-NH—⟨C₆H₄⟩—N(CH₃)₂ | 0.35 | 1.00** |
| CAPase | S-Bz-Cys-NH—⟨C₆H₄⟩—OH | 0.42 | 1.57 |
| | S-Bz-Cys-NH—⟨C₆H₄⟩—OCH₃ | 1.07 | 0.29 |
| *1 | Leu-NH—⟨C₆H₄⟩—N(CH₃)₂ | 0.56 | 1.00** |
| LAPase | Leu-NH—⟨C₆H₄⟩—OH | 0.43 | 1.52 |
| | Leu-NH—⟨C₆H₄⟩—OCH₃ | 0.75 | 1.98 |
| Chymotripsin | Bz-Tyr-NH—⟨C₆H₄⟩—N(CH₃)₂ | 0.61 | 0.123*** |

*1 γ-GtPase and LAPase measured on the same sera of a patient with hepatic disorder
*2 CAPase measured on the same sera of a pregnant woman
**Vmax indicated as the value given by the H₂N—⟨C₆H₄⟩—N(CH₃)₂ derivative being 1.00
***Vmax indicated in terms of the mol number of the substrate degraded (μ mole/minutes/mg · chymotripsin)

The method of this invention will be more fully disclosed by way of the following examples. However, it should be noted that this invention is not to be limiting by these examples.

EXAMPLE 1

To a solution of 2 g of sodium pentacyanoammineferroate in 20 ml of water were added 60 ml of 0.3% hydrogen peroxide and then 20 ml of 10% sodium hydrogencarbonate. Thereafter, 4 g of low molecular dextran was added thereto to prepare a color stock solution. A reaction stopping color solution was prepared by blending 1 ml of the color stock solution with 50 ml of 0.2M lactic acid buffer with pH 4.5 (containing 1% sodium chloride).

A substrate solution was prepared by dissolving 150 mg of L-glutamic acid γ-p-dimethylaminoanilide in a mixture of 6 ml of Methyl Cellosolve with 4 ml of 0.125 N hydrochloric acid.

A buffer was prepared by dissolving 0.8 g of glycylglycine, 0.5 g of sodium chloride and 0.5 g of Tween 80 (Trade name of a non-ionic surfactant, Atlas Powder Co., U.S.A.) in 100 ml of water and adjusting pH to 8.3 with 6N sodium hydroxide. The substrate solution was blended with the buffer to form a substrate buffer.

Into a test tube was placed 1 ml of the substrate buffer and, after heating to 37° C., 0.05 ml of human serum was added. Reaction was effected at 37° C. for 30 minutes and then 5 ml of the reaction stopping and color solution was added. The mixture was left at room temperature for 20 minutes to make color development. Absorbance at 660 nm was measured. On the other hand, another sample as a blank was prepared and treated by the same way as above except that 0.05 ml of water was added instead of the human serum and absorbance was similarly measured to obtain a blank value. Then, γ-GT-Pase activity in human serum was determined from the difference between the measured value and the blank value.

EXAMPLE 2

A substrate solution was prepared by dissolving 100 mg of S-benzyl-L-cysteine p-hydroxyanilide in a mixture of 3 ml of dioxane with 2 ml of 0.16 N hydrochloric acid. A substrate buffer was prepared by blending 100 ml of 0.1 M triethanolaminecitric acid buffer (pH 7.4) containing 1.25% of Tween 80 with the substrate solution.

Into a test tube was placed 1 ml of the substrate buffer and, after heating to 37° C., 0.05 ml of human serum was added. Reaction was effected at 37° C. for 30 minutes and then 5 ml of the reaction stopping and color solution prepared in Example 1 was added. The mixture was left at room temperature for 20 minutes to make color development. Absorbance at 660 nm was measured. On the other hand, another sample as a blank was prepared and treated by the same way as above except that 0.05 ml of water was added instead of the human serum and absorbance was similarly measured to obtain a blank value. Then, CPAase activity in human serum was determined from the difference between the measured value and the blank value.

EXAMPLE 3

A substrate solution was prepared by dissolving 100 mg of L-leucine p-hydroxyanilide in a mixture of 3 ml of Methyl Cellosolve with 2 ml of 0.25 N hydrochloric acid. A substrate buffer was prepared by blending 100 ml of 0.1 M triethanolamine - hydrochloric acid buffer (pH 8.0) containing 0.5% of Tween 80 with the substrate solution.

Into a test tube was placed 1 ml of the substrate buffer and, after heating to 37° C., 0.05 ml of human serum was added. Reaction was effected at 37° C. for 30 minutes and then 5 ml of the reaction stopping and color solution prepared in Example 1 was added. The mixture was left at room temperature for 20 minutes to make color development. Absorbance at 660 nm was measured. On the other hand, another sample as a blank was prepared and treated by the same way as above except that 0.05 ml of water was added instead of the human serum and absorbance was similarly measured to obtain a blank value. Then, LAPase activity in human serum was determined from the difference between the measured value and the blank value.

EXAMPLE 4

A substrate solution was prepared by dissolving 30 mg of N-benzyl-L-tyrosine p-dimethylaminoanilide in 5 ml of acetone. A substrate buffer was prepared by blending 100 ml of 0.1 M tris buffer solution (pH 7.8) (containing 5 mM calcium chloride, 1% Tween 80) with the substrate solution.

Into a test tube was placed 1 ml of the substrate buffer and, after heating to 37° C., 0.05 ml of a solution containing chymotrypsin was added. Reaction was effected at 37° C. for 30 minutes and then 5 ml of the reaction stopping and color solution prepared in Example 1 was added. The mixture was left at room temperature for 20 minutes to make color development. Absorbance at 660 nm was measured. On the other hand, another sample as a blank was prepared and treated by the same way as above except that 0.05 ml of water was added instead of the chymotripsin-containing solution and absorbance was similarly measured to obtain a blank value. Then, chymotripsin activity was determined from the difference between the measured value and the blank value.

What is claimed is:

1. In a method for the colorimetric determination of enzyme activity in a substance wherein the substance is treated with a mixture of a substrate and color reagent and is then colorimetrically analyzed, the improvement which comprises:

the substrate being an aromatic primary amine derivative selected from the group consisting of L-glutamic acid γ-p-dimethylaminoanilide,
L-glutamic acid γ-p-diethylaminoanilide,
L-glutamic acid γ-p-methoxyanilide,
L-glutamic acid γ-p-hydroxyanilide,
S-benzyl-L-cysteine p-dimethylaminoanilide,
S-benzyl-L-cysteine p-hydroxyanilide,
S-benzyl-L-cysteine p-methoxyanilide,
L-leucine p-dimethylaminoanilide,
L-leucine p-hydroxyanilide,
L-leucine p-methoxyanilide and
N-benzyl-L-tyrosine p-dimethylaminoanilide and said color reagent is an iron complex selected from the group consisting of sodium pentacyanoammineferroate and potassium pentacyanoammineferroate which is treated with a peroxide selected from the group consisting of sodium periodate, potassium periodate, potassium permanganate and hydrogen peroxide, and wherein said iron complex is further blended with an alkali metal hydrogen-carbonate and low molecular dextran.

2. A method according to claim 1 wherein said iron complex is a freeze-dried preparation further blended with sodium hydrogencarbonate and low molecular dextran.

3. A method according to claim 1 wherein said substance is human serum and a weakly acidic buffer with a pH of 3.0–7.0 is further present.

4. A method according to claim 1 wherein said aromatic primary amine derivative is a member selected from the group consisting of L-glutamic acid γ-p-dimethylaminoanilide,
L-glutamic acid γ-p-diethylaminoanilide,
L-glutamic acid γ-p-methoxyanilide,
L-glutamic acid γ-p-hydroxyanilide,
S-benzyl-L-cysteine p-dimethylaminoanilide,
S-benzyl-L-cysteine p-hydroxyanilide,
S-benzyl-L-cysteine p-methoxyanilide,
L-leucine p-dimethylaminoanilide,
L-leucine p-hydroxyanilide,
L-leucine p-methoxyanilide and
N-benzyl-L-tyrosine p-dimethylaminoanilide, and said iron complex is a freeze-dried preparation of a blend of sodium pentacyanoammineferroate treated with hydrogen peroxide, sodium hydrogencarbonate and low molecular dextran.

5. A diagnostic composition kit for determining an enzyme activity in a body fluid which comprises (a) an aromatic primary amine derivative as a substrate, (b) a freeze-dried preparation of a blend of an iron complex treated with a peroxide, an alkali metal hydrogencarbonate and low molecular dextran, and (c) a weakly acidic buffer with a pH of 3.0–7.0.

6. A method according to claim 1 wherein said aromatic primary amine derivative is a member selected from the group consisting of L-glutamic acid γ-p-dimethylaminoanilide,
L-glutamic acid γ-p-diethylaminoanilide,
L-glutamic acid γ-p-methoxyanilide,
L-glutamic acid γ-p-hydroxyanilide,
S-benzyl-L-cysteine p-dimethylaminoanilide,
S-benzyl-L-cysteine p-hydroxyanilide,
S-benzyl-L-cysteine p-methoxyanilide,
L-leucine p-dimethylaminoanilide,
L-leucine p-hydroxyanilide,
L-leucine p-methoxyanalide and
N-benzyl-L-tyrosine p-dimethylaminoanilide, said iron complex is sodium pentacyanoammineferroate and said peroxide is hydrogen peroxide.

* * * * *

UNITED STATES PATENT OFFICE
CERTIFICATE OF CORRECTION

Patent No. 4,116,774        Dated Sept. 26, 1978

Inventor(s) Sadamasa Minato, A. Hattori, et al

It is certified that error appears in the above-identified patent and that said Letters Patent are hereby corrected as shown below:

In the heading of the patent [75] should read as follows:

[75] Inventors: Sadamasa Minato; Atsushi Hattori; Yoshihiko Baba; Yuichiro Yabe; Seigo Ueda, all of Tokyo , Japan Signed and Sealed this Twenty-sixth Day of December 1978

[SEAL]

Attest:

RUTH C. MASON
Attesting Officer

DONALD W. BANNER
Commissioner of Patents and Trademarks